United States Patent [19]

Didillon

[11] Patent Number: 5,672,801
[45] Date of Patent: Sep. 30, 1997

[54] CATALYST REGENERATION PROCESS AND USE OF THE CATALYST IN HYDROCARBON CONVERSION PROCESSES

[75] Inventor: Blaise Didillon, Rueil Malmaison, France

[73] Assignee: Institut Francais Du Petrole, Rueil Malmaison, France

[21] Appl. No.: 692,470

[22] Filed: Aug. 6, 1996

Related U.S. Application Data

[62] Division of Ser. No. 573,658, Dec. 18, 1995, Pat. No. 5,573,988, which is a continuation of Ser. No. 348,235, Nov. 28, 1994, abandoned.

[30] Foreign Application Priority Data

Nov. 26, 1993 [FR] France ................. 93 14281

[51] Int. Cl.$^6$ ............... C07C 5/333; B01J 38/44
[52] U.S. Cl. ............... 585/660; 585/661; 585/662; 585/663; 585/627; 585/631; 208/140; 503/37
[58] Field of Search ............... 585/616, 661, 585/662, 663, 627, 631, 629, 694, 698, 660; 502/37; 208/140

[56] References Cited

U.S. PATENT DOCUMENTS

| | | | |
|---|---|---|---|
| 3,673,090 | 6/1972 | Waldbillig et al. | 252/45 |
| 3,882,031 | 5/1975 | Askew et al. | |
| 4,097,474 | 6/1978 | Askew et al. | |
| 4,119,549 | 10/1978 | Davis. | |
| 4,192,771 | 3/1980 | Burbridge et al. | 252/415 |
| 4,225,488 | 9/1980 | Horodysky et al. | 252/45 |
| 4,284,520 | 8/1981 | Bolle et al. | 568/21 |
| 4,444,895 | 4/1984 | Fung et al. | 502/37 |
| 4,584,113 | 4/1986 | Walsh | 252/45 |
| 4,739,036 | 4/1988 | Colvin et al. | 528/389 |
| 4,851,380 | 7/1989 | Van Leirsburg et al. | 502/37 |
| 4,855,269 | 8/1989 | Mohr | 502/37 |
| 4,872,970 | 10/1989 | Boyle | 208/140 |
| 4,983,558 | 1/1991 | Born et al. | |
| 5,133,889 | 7/1992 | Born et al. | |
| 5,135,670 | 8/1992 | Johnson et al. | 252/45 |
| 5,232,623 | 8/1993 | Shaw | 252/193.18 |
| 5,286,395 | 2/1994 | Born et al. | 252/45 |
| 5,338,468 | 8/1994 | Arvizzigno et al. | 252/45 |
| 5,403,960 | 4/1995 | Kadkhodayan et al. | 568/21 |
| 5,410,088 | 4/1995 | Harris et al. | |

FOREIGN PATENT DOCUMENTS

| | | |
|---|---|---|
| 130850 | 2/1984 | European Pat. Off. |
| 0 201 197 | 11/1986 | European Pat. Off. |
| 0 258 168 | 3/1988 | European Pat. Off. |
| 0 274 934 | 7/1988 | European Pat. Off. |
| 1 211 610 | 8/1958 | France. |
| 1 359 677 | 1/1963 | France. |
| 1 131 265 | 5/1963 | France. |
| 2 365 629 | 4/1978 | France. |
| 2 627 104 | 2/1988 | France. |
| 734 249 | 5/1980 | U.S.S.R. ............ C10M 135/04 |
| 748 694 | 6/1953 | United Kingdom. |
| 1 067 378 | 5/1967 | United Kingdom. |
| 1 404 714 | 9/1975 | United Kingdom. |

OTHER PUBLICATIONS

Chemical Abstract, vol. 100(18), Abstract No. 14201m, 20 Apr. 1984.

*Primary Examiner*—Glenn A. Caldarola
*Assistant Examiner*—Bekir L. Yildirim
*Attorney, Agent, or Firm*—Millen, White, Zelano, & Branigan, P.C.

[57] ABSTRACT

The present invention concerns a regeneration process for a catalyst containing at least one metallic element selected from the group formed by platinum, palladium, ruthenium, rhodium, osmium, iridium and nickel, preferably platinum, on a refractory oxide based support, which has been deactivated by coke deposition. The regeneration process is characterised in that said regeneration consists of treatment with a gas containing at least chlorine and molecular oxygen, at a temperature between 20° C. and 800° C. and a total gas flow rate, expressed in litres of gas per hour and per gram of catalyst, of between 0.05 and 20. The process at least restores the initial catalytic properties of the catalyst.

15 Claims, No Drawings

CATALYST REGENERATION PROCESS AND USE OF THE CATALYST IN HYDROCARBON CONVERSION PROCESSES

This is a division of the application Ser. No. 09/573,658 filed Dec. 18, 1995, U.S. Pat. No. 5,573,988, which is a continuation of Ser. No. 08/348,235, filed Nov. 28, 1994 abandoned.

The present invention concerns a regeneration process for a catalyst containing at least one metallic element selected from the group formed by platinum, palladium, ruthenium, rhodium, osmium, iridium and nickel, preferably platinum, on a refractory oxide based support, which has been deactivated by coke deposition. The regeneration process is such that it produces an essentially uncoked catalyst using a controlled coke combustion process which at least restores the performance of the catalyst, ie., the activity, selectivity and stability of the regenerated catalyst are at least equal to that of the initial uncoked catalyst. The present invention is of particular application to regenerating dehydrogenation and dehydrocyclization catalysts for hydrocarbon feedstocks comprising mainly paraffins containing 3 to 8, in particular 3 to 5 carbon atoms per molecule.

Dehydrogenation catalysts are conventionally composed of platinum, optionally tin, optionally an alkali metal, and optionally a halogenated compound on a refractory oxide such as alumina. Platinum and tin based supported catalysts for dehydrogenating paraffin hydrocarbons are described in United States patents U.S. Pat. Nos. 3,531,543 and 3,998,900. Dehydrogenation reactions are endothermic and reversible. The conversion ratios are limited by the thermodynamic equilibrium conditions. Severe conditions favourably displace the dehydrogenation reaction towards olefin formation, but also favour undesirable secondary coke-forming and/or cracking reactions. The presence of coke is the main source of dehydrogenation catalyst deactivation. In certain instances, sintering and/or poisoning of the metallic phase can also result in loss of catalyst performance. A regeneration process is thus necessary in order to restore the initial catalytic properties of the catalyst.

In the case of dehydrogenation processes, the deactivated catalysts are regenerated using a process which includes a combustion step for the coke present on the catalyst by treating the latter with oxygen at a high temperature between 400° C. and 600° C. to burn off the hydrocarbon species constituting the coke. However, agglomeration of metallic particles during this step reduces the active surface area of the metal and thus reduces the activity and stability of the regenerated catalyst. As a consequence, a metallic phase redispersion step is required following the combustion step. For this type of catalyst, this is conventionally an oxychlorination step which is carried out by treating the catalyst with a chlorine-containing gas in the presence of oxygen and, if necessary, water, using any technique known to the skilled person.

United States patent U.S. Pat. No. 5,087,792 describes a three step regeneration process for a coked dehydrogenation catalyst. The first step consists in burning off the coke by treating the catalyst with a gas containing oxygen at a temperature of between 471° C. and 538° C. The second step consists in drying the catalyst, for example in dry air between 426° C. and 593° C. Finally, the third step consists in redispersing the platinum on the catalyst surface by treatment with a chlorine-containing gas [0.01 to 0.2% (molar) of chlorine in air].

United States patent U.S. Pat. No. 4,359,400 describes the regeneration of a coked platinum based catalytic reforming catalyst which is carried out in a plurality of steps. The first step consists in burning off the coke by treating the catalyst with a gas containing oxygen at a temperature close to 482° C. The second step consists in reducing the catalyst by treatment in hydrogen at about 482° C. The third step consists in treating the catalyst with a gas containing a hydrogen halide at the same temperature. The fourth step consists in treating the catalyst with a gas containing elemental halogen at about 482° C. Finally, the catalyst is reduced in hydrogen at 482° C. in the fifth step.

United States patent U.S. Pat. No. 3,875,049 describes the regeneration of a deactivated platinum and tin based catalytic reforming catalyst using a two step process. The first, coke combustion, step is carried out by treatment with a gas containing oxygen at 750° F. In a second step, the catalyst is treated with a gas containing oxygen, carbon tetrachloride and water to reactivate the catalyst.

These examples show that regeneration of catalysts containing at least one metallic element selected from the group formed by platinum, palladium, ruthenium, rhodium, osmium, iridium and nickel, preferably platinum, on a refractory oxide based support, is well known but it requires a large number of steps. These steps are most often carried out in at least two different reactors or in at least two different zones in the same reactor, with concomitant disadvantages regarding the industrial process.

The object of the present invention is to provide a process for the regeneration of a catalyst containing at least one metallic element selected from the group formed by platinum, palladium, ruthenium, rhodium, osmium, iridium and nickel, preferably platinum, on a refractory oxide based support, ie., on a support comprising at least one refractory oxide, said catalyst having been deactivated by coke deposition. The regeneration process is such that it produces an essentially coke-free catalyst using a controlled coke combustion process which at least restores the catalytic performance, ie., the activity, selectivity and stability of the regenerated catalyst are at least equal to those of the initial coke-free catalyst.

The support for the catalyst which is regenerated using the process of the invention contains at least one refractory oxide selected from the group formed by the following elements: alumina, titanium oxides, zinc oxides, magnesium oxides and chromium oxides. Alumina is the preferred support. The specific surface area of the support is advantageously between 50 and 600 $m^2/g$, preferably between 100 and 400 $m^2/g$.

The catalyst may also contain an additional element selected from the group formed by the following elements: germanium; tin; indium; titanium; rhenium; tungsten; chromium; iron; an alkali metal, ie., an element from group 1 A of the periodic classification of the elements, such as potassium; a halogen, ie., an element from group VIIA of the periodic classification of the elements, such as chlorine; or other elements such as boron, carbon, nitrogen, oxygen, silicon, phosphorus, sulphur, arsenic, selenium and tellurium.

Prior to the regeneration process, the catalyst may undergo treatments to eliminate certain catalyst poisons. Treatment with hydrogen, for example, to eliminate sulphur adsorbed on the catalyst, may be carried out before the combustion step.

In the regeneration process of the invention, the coked catalyst is regenerated in a single step to essentially completely eliminate the coke and essentially restore the initial properties of the catalyst. Said process thus comprises a single treatment step with a gas containing at least chlorine and molecular oxygen, at a temperature generally between 20° C. and 800° C. and a gas flow rate, expressed in liters of gas per hour per gram of catalyst, of generally between 0.05 and 20, preferably between 0.5 and 10. The single step in the process of the invention preferably includes a stage at which the temperature is kept between 250° C. and 600° C., said temperature remaining constant or otherwise during this stage, for a defined period whose duration depends on the other operational conditions of the process. If the temperature remains constant for a defined period during this stage, it is said to contain a temperature plateau.

Two embodiments of the process of the invention will be described below.

In a first embodiment, said catalyst is brought into contact with said gas at room temperature and the temperature is then raised in progressive and controlled fashion. Said temperature is then kept at a plateau of between 250° C. and 600° C. in the gas stream, the temperature remaining constant or otherwise while remaining in the gas stream, to result in essentially complete decoking of said catalyst. In this embodiment, the temperature gradient is generally between 1 and 10° C./min, preferably between 1 and 5° C./min.

In a second embodiment of the process of the invention, said catalyst is brought directly into contact with said gas at a temperature of between 250° C. and 600° C., the temperature remaining constant or otherwise for a defined period while remaining in the gas stream, to result in essentially complete decoking of said catalyst.

The operating conditions are generally as follows regardless of the embodiment employed for the process of the invention:

The catalyst regeneration gas contains at least oxygen and chlorine. It may optionally also contain at least one diluent such as nitrogen. The oxygen content in said gas is between 0.3% and 51% (molar), preferably between 1% and 22% (molar). The chlorine content in said gas, expressed as a molar % of chlorine, is between 0.02% and 3%, preferably between 0.1% and 1%. Said gas may, for example, be air to which a specific quantity of a chlorinated compound is added. The chlorinated compound which is generally used as a source of chlorine can be elemental chlorine or a chlorinated carbon-containing compound such as carbon tetrachloride, chloroform or 1,2-dichloropropane.

Regardless of the embodiment employed, said process always produces a regenerated catalyst, ie., a catalyst which is essentially completely free of coke and which has essentially recovered its initial properties, ie., its properties prior to any catalytic use.

Following regeneration in accordance with the invention, the catalyst can then undergo different treatments such as calcination or reduction under conditions which are known to the skilled person.

The following examples illustrate the invention without limiting its scope.

EXAMPLE 1 (comparative)

Dehydrogenation catalyst A was prepared using conventional methods as described in European patent application EP-A-562 906. This catalyst was composed of 0.6% by weight of platinum, 1.0% by weight of potassium, 0.38% of tin and 1.09% of chlorine.

A used catalyst A containing 22.1% of carbon from an isobutane dehydrogenation unit operating under the conditions described in European patent application EP-A-559, 509 was used. It was regenerated using the following process:

1) Used catalyst A was treated at 470° C. in nitrogen containing 0.5% by volume of oxygen to produce carbon monoxide in the exit gases, and the temperature was progressively increased to 530° C. to complete the combustion (temperature increase of 2° C./min).

2) Used catalyst A, having undergone the combustion step, was treated with a gas containing 23 molar % of oxygen and 0.3 molar % of chlorine (in the form of 1,2-dichloropropane) at 530° C. for 2 hours.

The catalyst obtained was termed catalyst B.

EXAMPLE 2 (according to the invention)

Used catalyst A containing 22.1% of carbon from an isobutane dehydrogenation unit operating under the conditions described in European patent application EP-A-559, 509, was regenerated using the following process:

Used catalyst A was treated in a current of nitrogen containing 20 molar % of oxygen and 0.3 molar % of chlorine in the form of 1,2-dichloropropane. The gas flow rate was 1 litre of gas per gram of catalyst per hour. During combustion, the temperature was increased from 20° C. to 530° C. at a rate of 2 ° C./min. The temperature was then held at 530° C. for 2 hours, keeping the gas flow rate constant.

The catalyst obtained was termed catalyst C.

EXAMPLE 3

Catalysts A, B and C were used to dehydrogenate a pure isobutane feedstock (99.9% isobutane and 0.1% n-butane) in an isothermal tubular reactor operating in descending flux mode at atmospheric pressure. The catalyst was first reduced for 2 hours in hydrogen at 530° C. Isobutane was then injected at a flow rate which corresponded to a molar ratio of hydrogen to hydrocarbon of 1 and at a space velocity of $14h^{-1}$ (expressed in grams of hydrocarbon per hour per gram of catalyst). The temperature was held at 560° C. for 1 hour, then increased to 580° C. The gaseous effluents were analysed on line using gas phase chromatography.

The results obtained under these conditions are summarised in Table 1.

TABLE 1

| Catalyst | Temperature (°C.) | Duration (h) | $iC_4$ conversion (wt %) | $iC_4^-$ selectivity (wt %) | $iC_4^-$ yield (wt %) |
| --- | --- | --- | --- | --- | --- |
| A | 560 | 1 | 41.5 | 90.5 | 37.6 |
|   | 580 | 2 | 48.3 | 89.6 | 43.3 |
|   | 580 | 3 | 48.7 | 89.7 | 42.2 |
| B | 560 | 1 | 41.4 | 88.6 | 36.7 |
|   | 580 | 2 | 48.0 | 88.5 | 42.5 |
|   | 580 | 3 | 47.5 | 88.7 | 42.1 |
| C | 560 | 1 | 43.0 | 90.6 | 38.9 |
|   | 580 | 2 | 49.9 | 87.7 | 43.8 |
|   | 580 | 3 | 50.4 | 87.8 | 44.3 |

The catalyst which had been regenerated in accordance with the invention (catalyst C) thus had identical, or even superior, properties to those of the original catalyst (catalyst A) or those of the catalyst which had been regenerated using prior art techniques (catalyst B). The single step regeneration process of the invention thus restores a coked catalyst to its original state.

I claim:

1. A process for the dehydrogenation or dehydrocyclization of a hydrocarbon feedstock comprising paraffins of 3 to 8 carbon atoms per molecule, comprising contacting said feedstock with a catalyst containing at least one metallic element selected from the group formed by platinum, palladium, ruthenium, rhodium, osmium, iridium and nickel on a refractory oxide based support, said catalyst having been deactivated by coke deposition and regenerated by a process comprising burning off of deposited coke, and conducting oxychlorination, by simultaneously effecting oxychlorination whenever burning off deposited coke, by treating the catalyst with a gas containing at least chlorine and molecular oxygen, at a temperature generally between 20° C. and 800° C. and a total gas flow rate, expressed in liters of gas per hour per gram of catalyst, of between 0.05 and 20.

2. A process according to claim 1, wherein the regeneration includes a stage in which the temperature is kept between 250° C. and 600° C.

3. A process according to claim 1, wherein said regeneration comprises treating the catalyst containing at least chlorine and molecular oxygen, by bringing the gas and the catalyst into contact at room temperature then increasing the temperature in a progressive and controlled fashion, at a rate of between 1 and 10 ° C./minute, followed by a stage where the temperature is kept between 250° C. and 600° C.

4. A process according to claim 1, wherein said regeneration comprises treating the catalyst with a gas containing at least chlorine and molecular oxygen, by bringing the gas and the catalyst directly into contact at a temperature of between 250° C. and 600° C.

5. Process according to claim 1 wherein the molecular oxygen content in said gas is between 0.3% and 51% (molar) and the chlorine content in said gas, expressed as a molar % of chlorine, is between 0.02% and 3%.

6. Process according to claim 5, wherein the molecular oxygen content of said gas is between 1% and 22% (molar) and the chlorine content in said gas, expressed as a molar % of chlorine, is between 0.1% and 1%.

7. Process according to claim 1, wherein said metallic element is platinum.

8. Process according to claim 1, wherein said support is alumina.

9. Process according to claim 1, wherein said catalyst further comprises at least one additional element selected from the group formed by the following elements: germanium, tin, indium, titanium, rhenium, tungsten, chromium, iron, an alkali metal, a halogen, boron, carbon, nitrogen, oxygen, silicon, phosphorus, sulphur, arsenic, selenium and tellurium.

10. A process for the dehydrogenation or dehydrocyclization of a hydrocarbon feedstock comprising paraffins of 3 to 8 carbon atoms per molecule, comprising contacting said feedstock with a dehydrogenation or dehydrocyclization catalyst deactivated by coke deposition, and regenerated by burning off deposited coke and conducting oxychlorination, by simultaneously conducting oxychlorination whenever burning off deposited coke.

11. A process for the dehydrogenation or dehydrocyclization of a hydrocarbon feedstock comprising paraffins of 3 to 8 carbon atoms per molecule, comprising contacting said feedstock with a dehydrogenation or dehydrocyclization catalyst deactivated by coke deposition, and regenerated by calcining said catalyst in the presence of a gas containing oxygen and chlorine in amounts effective to redistribute any agglomerated catalyst metals, with the proviso that calcining of the catalyst is not conducted in the absence of the gas containing oxygen and chlorine.

12. A process according to claim 11, wherein the amount of oxygen is 0.3 - 51 molar % and the amount of chlorine is 0.02 - 3 molar %.

13. A process according to claim 1, wherein prior to burning off of coke, the catalyst is treated with hydrogen to eliminate sulfur adsorbed thereon.

14. A process according to claim 10, wherein prior to burning off of coke, the catalyst is treated with hydrogen to eliminate sulfur adsorbed thereon.

15. A process according to claim 11, wherein prior to burning off of coke, the catalyst is treated with hydrogen to eliminate sulfur adsorbed thereon.

* * * * *